United States Patent [19]

Matsumura et al.

[11] 4,339,585

[45] Jul. 13, 1982

[54] METHOD FOR THE PRODUCTION OF 2-HYDROXYMETHYL-3,4,5-TRIHYDROXY PIPERIDINE AND THE CORRESPONDING N-METHYL DERIVATIVE

[75] Inventors: Shingo Matsumura; Hiroshi Enomoto; Yoshiaki Aoyagi; Yoji Ezure; Yoshiaki Yoshikuni; Masahiro Yagi, all of Kyoto, Japan

[73] Assignee: Nippon Shinyaku Co., Ltd., Japan

[21] Appl. No.: 959,163

[22] Filed: Nov. 9, 1978

[30] Foreign Application Priority Data

Nov. 10, 1977 [JP] Japan .............................. 52/135505
Nov. 10, 1977 [JP] Japan .............................. 52/135506

[51] Int. Cl.$^3$ ........................................... C07D 211/46
[52] U.S. Cl. ................................. 546/242; 435/122
[58] Field of Search ................... 546/242; 195/12, 101, 195/80 R

[56] References Cited

U.S. PATENT DOCUMENTS 4,103,083 7/1978 Ogawa et al. ................ 195/80 R X

OTHER PUBLICATIONS

Ishida, N. et al., *J. Antibiotics*, Ser. A20, 62-65, (I) and 66-71 (II), (1967).
Inouye, S. et al., *Tetrahedron*, 24, 2125, (1968).
March, J., *Advanced Organic Chemistry*, McGraw Hill, New York, 1968, pp. 668-670.

*Primary Examiner*—Richard A. Schwartz
*Attorney, Agent, or Firm*—Jacobs & Jacobs

[57] ABSTRACT

Moranoline, or 2-hydroxymethyl-3,4,5-trihydroxy piperidine, is prepared by directly reducing an actinomycetes culture solution containing nojirimycin, followed by isolation, as for example, through the utilization of an ion exchange resin. The corresponding N-methyl derivative can be obtained through the addition of formaldehyde to the culture solution prior to the reduction.

6 Claims, 2 Drawing Figures

METHOD FOR THE PRODUCTION OF 2-HYDROXYMETHYL-3,4,5-TRIHYDROXY PIPERIDINE AND THE CORRESPONDING N-METHYL DERIVATIVE

DETAILED DESCRIPTION

Figure 2:
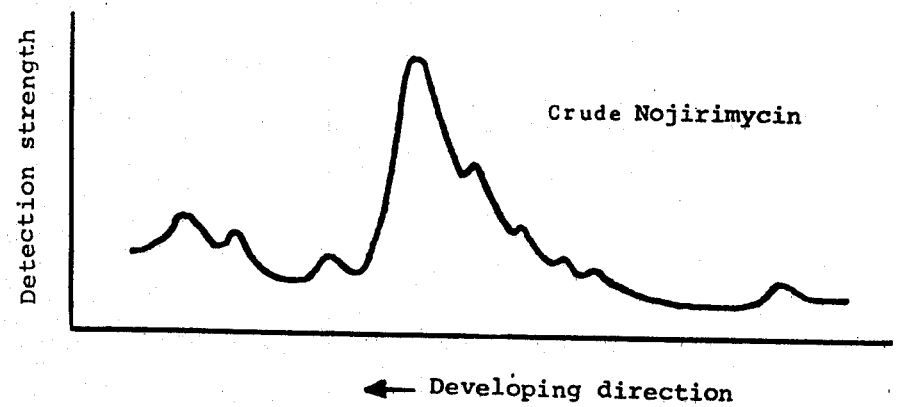

The present invention relates to a method for the production of moranoline and its corresponding N-methyl derivative which can be represented by the formula:

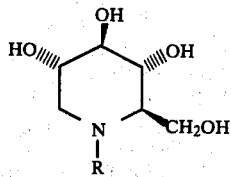

wherein R is hydrogen or methyl, and salts thereof.

Moranoline (R=H) is a naturally occurring substance which has been isolated from the root bark of mulberry and is known to have the medicinally useful effect of reducing blood sugar levels in humans and other animals. Yagi et al., J. Ag. Chem. Soc. Japan, 50, 571 (1976) and U.S. Pat. No. 4,065,562. The corresponding N-methyl derivative has also been demonstrated to have the same property.

Apart from extracting moranoline from plant material, the only other general method for its production involves the reduction of 2-hydroxymethyl-3,4,5,6-tetrahydroxy piperidine utilizing for example catalytic hydrogenation with a platinum catalyst or chemical reduction with sodium borohydride. Inoue et al., Tetrahedron, 24, 2125 (1968). 2-Hydroxymethyl-3,4,5,6-tetrahydroxy piperidine is the antibiotic nojirimycin and is produced through fermentation techniques from various actinomycetes (see Japanese published applications Nos. 760/1968 and 5033/1970). Nojirimycin is, however, extremely unstable and not only decomposes in acidic environments but even decomposes under neutral conditions. Although several cumbersome techniques such as ion exchange column chromatography and formation of a sulfurous acid adduct have been utilized, the loss in the course of purification is often 50% or more. Moreover, the reduction of nojirimycin utilizing for example a platinum catalyst results in a further loss of 50% or more. Consequently, the production of moranoline from nojirimycin requires several cumbersome operations and produces overall yields of only 15 to 20%. The corresponding N-methyl moranoline has heretofore been produced through N-methylation of moranoline itself and is thus liable to all of the disadvantages inherent in the production of this starting material.

It has now been found that it is possible to avoid these difficulties through reduction of a nojirimycin-containing culture solution of actinomycetes, in the case of the N-methyl derivative, after addition of a source of formaldehyde. In the case of moranoline, for example, a yield five times higher than that heretofore obtainable is thus possible, the increase in yield being accompanied by elimination of numerous cumbersome extraction and isolation steps.

In the case of moranoline itself, the reduction is preferably conducted by catalytic hydrogenation, utilizing for example metal catalysts such as manganese, zinc, cobalt, copper and the like. Most preferable is the use of Raney nickel as the reduction catalyst. Following reduction, the culture solution is subjected to purification, preferably utilizing an ion exchange resin. This technique makes it possible to produce moranoline in an almost quantitative yield. One of the surprising discoveries in connection with this process is the fact that if nojirimycin is extracted from a culture solution according to conventional techniques, numerous metabolites or decomposition products are simultaneously removed and greatly complicate the purification operations. These complications are particularly significant in view of the inherent lack of stability of nojirimycin. The reduction operation of the present invention not only effects the desired transformation of nojirimycin into moranoline but also denatures these undesired side effects so that when moranoline is isolated as by ion exchange treatment, the level of these undesired side effects is extremely low and they can be easily removed through simple salt formation, utilizing a mineral acid or organic acid in the conventional manner. Thus by direct reduction of the nojirimycin-containing culture, it is not only possible to increase the yield of the desired moranoline, it is also possible to eliminate the effect of undesired side effects which heretofore have hampered subsequent purification.

Figure 1:
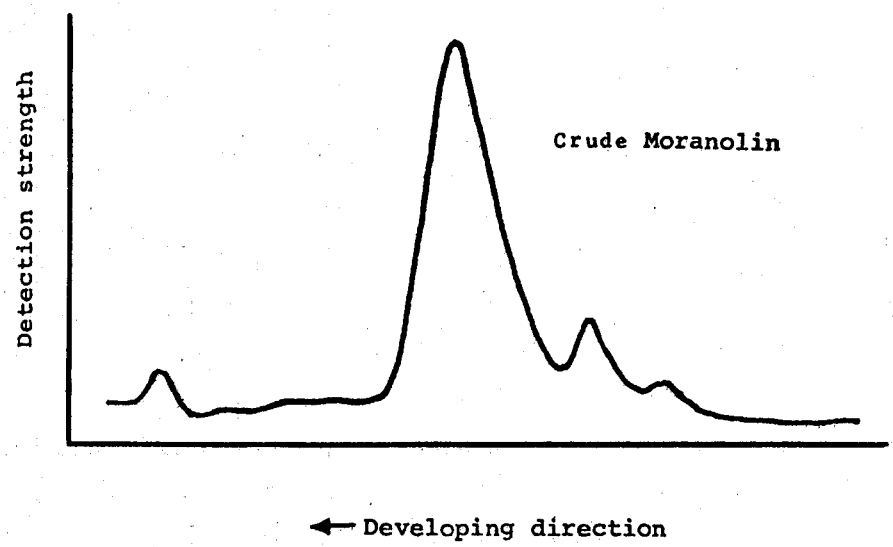

As will be seen from the accompanying FIGS. 1 and 2, which are thin layer chromatograms of crude moranoline and crude nojirimycin, respectively (utilizing silica gel as the absorbant and ethanol:water:-chloroform (4:2:1) with a hydrogen flame ionization detector), the starting material is in admixture with a variety of impurities whereas the moranoline obtained according to the present invention contains significantly fewer impurities.

As noted above, numerous of the known reduction catalysts can be employed, nickel catalyst being preferred. Commercially available industrial Raney nickel catalysts are completely satisfactory.

In the case of N-methyl moranoline (R=CH$_3$), there is first added a source of formaldehyde. This may be an aqueous solution of formaldehyde, paraformaldehyde, formic acid salts or the like. In addition to the utilization of catalytic reduction, chemical reduction can also be employed, utilizing for example sodium borohydride. Following addition of the formaldehyde, reduction is carried out as previously described and the product then isolated again through utilization of an ion exchange resin.

It will be immediately apparent to those skilled in the art that certain modifications are possible, as for example the utilization of the sulfurous acid adduct of nojirimycin, a stabilized derivative. In the case of the preparation of N-methyl moranoline, one could of course utilize purified nojirimycin, although here the various disadvantages attendant to this isolation would be present. Although ion exchange has proved to be the most advantageous and simplest of isolation methods, other equivalent methods for extracting and isolating water soluble substances could be substituted, as for example adsorption on activated carbon, partition chromatography, countercurrent distribution, adsorption chromatography utilizing polyamides, porous resins or the like, chromatography employing Sephadex or derivatization, as for example formation of esters followed by extraction.

The following examples will serve to further typify the nature of this invention but should not be construed as a limitation on the scope thereof, the scope being defined solely by the appended claims.

EXAMPLE 1

A nojirimycin-producing actinomycetes belonging to Streptomyces is inoculated into 5 l of a liquid medium consisting of 2% of starch, 1% of soybean powder, 0.05% of KCl, 0.05% of $MgSO_4.7H_2O$, 0.5% of NaCl, and 0.35% of $CaCO_3$, and a shaking incubation is carried out at 27° C. for 3 hours in an aerating manner. After completion of the incubation, 500 g of High-Flow Super-Cell is added, followed by filtration to obtain 4.4 l of a filtrate. The content of nojirimycin in this filtrate was 500 μg/ml according to a biological assay employing [β-glucosidase (Niwa et al: Agr. Biol. Chem., 34, 966 (1970)].

To 500 ml of the instant culture solution is added about 10 ml of a commercially available, industrial Raney nickel, and stirring is carried out in a stream of hydrogen at ordinary temperature and under atmospheric pressure. In 6 hours, about 200 ml of hydrogen gas has been absorbed, and this is stopped. The catalyst is separated by filtration, and the resulting filtrate is passed through a column containing 300 ml of Dowex 1×2 (OH), and the resulting effluent is further passed through a column containing 200 ml of Dowex 50 W×4 (H). The column is washed with 2 l of water, followed by eluting the adsorbed substances with 0.5% aqueous ammonia. The resulting elute is concentrated and brought to dryness under reduced pressure, and a pale yellow-brown crystal remains. Yield: 280 mg. The thin-layer chromatogram of this product is shown in FIG. 1. Recrystallization from methanol gives 218 mg of purified moranoline (i).

m.p.: 203°–205°, $[\alpha]_D^{24}=44.6°$ (water). Yield: 87%.

EXAMPLE 2

179 mg of nojirimycin is dissolved in 20 ml of water, followed by adding 1 ml of formalin, adding about 0.5 ml of Raney nickel catalyst and stirring in a hydrogen stream, at ordinary temperature, under atmospheric pressure, for 3 hours. After completion of the reaction, the catalyst is separated by filtration; the resulting filtrate is passed through a column containing about 100 ml of Dowex 50 W×4 (H); and after washing the column, the resulting adsorbed substances are eluted with 1% aqueous ammonia. The resulting elute is brought to dryness under reduced pressure, and the remaining colorless crystal is recrystallized from ethanol to obtain N-methyl moranoline.

m.p.: 141°–142°, $[\alpha]_D^{24}=15.5°$ (water). Yield: 161 mg (91%).

EXAMPLE 3

179 mg of nojirimycin is dissolved in 20 ml of a 50% water-containing ethanol, followed by adding 1 ml of formalin, adding 100 mg of palladium on carbon catalyst and carrying out a catalytic reduction at ordinary temperature and under atmospheric pressure. The subsequent treatments are carried out in the same manner as in Example 2 to obtain 144 mg (81%) of N-methyl moranoline.

EXAMPLE 4

179 mg of nojirimycin is dissolved in 20 ml of water, followed by adding 1 ml of formalin, adding 100 mg of platinum on carbon catalyst and carrying out a catalytic reduction at ordinary temperature and under atmospheric pressure. The following treatments are carried out in the same manner as in Example 2 to obtain 150 mg (85%) of N-methyl moranoline.

EXAMPLE 5

261 mg of nojirimycin sulfurous acid adduct is suspended in 30 ml of water, followed by adding 1 ml of formalin and about 2 ml of Raney nickel catalyst and carrying out a catalytic reduction at ordinary temperature, under atmospheric pressure, for 6 hours.

The followig treatments are carried out in the same manner as in Example 2 to obtain 138 mg (78%) of N-methyl moranoline.

EXAMPLE 6

20 ml of formalin is added to 500 ml of a culture solution of a nojirimycin-producing actinomycetes containing about 500 μg/ml of nojirimycin, followed by adding about 10 ml of a commercially available, industrial Raney nickel catalyst and carrying out a catalytic reduction at ordinary temperature and under atmospheric pressure. About 1.3 l of hydrogen gas is absorbed in 6 hours and the gas feed is stopped. The catalyst is separated by filtration; the resulting filtrate is passed through a column containing about 500 ml of Dowex 1×2 (OH); and the resulting effluent is successively passed through a column containing 200 ml of Dowex 50 W×4 (H). The latter column is washed with 2 l of a 50% water-containing methanol, followed by eluting the resulting adsorbed substances with 0.5% aqueous ammonia and bringing the resulting elute to dryness under reduced pressure. To the remaining substance (280 mg) is added 250 mg of anhydrous p-toluenesulfonic acid, followed by adding 10 ml of isopropanol and heating, to precipitate crystal; yield: 344 mg.

The resulting mother liquor of crystal is brought to dryness under reduced pressure, followed by dissolving the remaining substances in water and again subjecting to a column treatment by means of Dowex 1×2 and Dowex 50 W×4, and adding 50 mg of anhydrous p-toluenesulfonic acid to the resulting extract, to precipitate 83 mg of a second crystal. In such a manner, p-toluenesulfonate of N-methyl moranoline (overall yield: 427 mg (87%)) is obtained.

m.p.: 198°–199° $[\alpha]_D^{24}=12.2°$ (methanol).

What is claimed is:

1. Process for the preparation of 2-hydroxymethyl3,4,5-trihydroxy piperidine which comprises subjecting a nojirimycin-producing actinomycetes culture containing nojirimycin to catalytic reduction with a metal catalyst until substantially all of said nojirimycin is converted to 2-hydroxymethyl-3,4,5-trihydroxy piperidine and isolating said 2-hydroxymethyl-3,4,5-trihydroxy piperidine by ion exchange chromatography.

2. The process according to claim 1 wherein said reduction is effected with Raney nickel.

3. Process for the preparation of 2-hydroxymethyl-3,4,5-trihydroxy N-methyl piperidine which comprises adding a source of at least an equivalent amount of formaldehyde to a nojirimycin-producing actinomycetes culture containing nojirimycin, thereafter catalytically or chemically reducing said culture, and isolating said 2-hydroxymethyl-3,4,5-trihydroxy-N-methyl piperidine.

4. The process according to claim 3 wherein said reduction is effected with Raney nickel.

5. The process of claim 3 wherein said reduction is effected by catalytic hydrogenation over a palladium or platinum catalyst.

6. The process of claim 3 wherein said 2-hydroxymethyl-3,4,5-trihydroxy-N-methyl piperidine is isolated by ion exchange chromatography.

* * * * *